United States Patent [19]

Thompson et al.

[11] Patent Number: 4,483,778

[45] Date of Patent: Nov. 20, 1984

[54] PEROXYGEN BLEACH ACTIVATORS AND BLEACHING COMPOSITIONS

[75] Inventors: James E. Thompson; Charles D. Broaddus, both of Cincinnati, Ohio

[73] Assignee: The Procter & Gamble Company, Cincinnati, Ohio

[21] Appl. No.: 564,786

[22] Filed: Dec. 22, 1983

[51] Int. Cl.$^3$ .......................... C11D 7/38; C11D 7/54
[52] U.S. Cl. ........................................ 252/94; 252/91; 252/95; 252/99; 252/106; 252/174; 252/174.13; 252/182; 252/186.31; 252/186.38; 260/404; 548/312; 560/183; 560/187; 560/223; 560/227; 560/228; 564/155; 564/158
[58] Field of Search .............. 252/182, 186.25, 186.31, 252/186.38, 91, 174.13, 174, 95, 94, 99, 106; 560/228, 227, 187, 183, 223; 548/312; 260/404; 564/155, 158

[56] References Cited

U.S. PATENT DOCUMENTS

| | | |
|---|---|---|
| 362,812 | 3/1882 | Gray et al. . |
| 433,499 | 10/1882 | Chung . |
| 3,075,921 | 1/1963 | Brocklehurst .............. 252/186.26 X |
| 3,130,165 | 4/1964 | Brocklehurst .................... 252/99 X |
| 3,245,913 | 4/1966 | Matzner . |
| 3,338,839 | 8/1967 | MacKellar et al. . |
| 3,368,943 | 2/1968 | Gilbert et al. .................... 252/99 X |
| 3,553,140 | 1/1971 | Linder et al. ...................... 252/95 X |
| 3,637,339 | 1/1972 | Gray .......................... 252/174.13 X |
| 3,686,127 | 8/1972 | Boldingh . |
| 3,822,114 | 7/1974 | Montgomery et al. ..... 252/186.38 X |
| 3,960,743 | 6/1976 | Nakagawa et al. . |
| 3,969,257 | 7/1976 | Murray ............................. 252/99 X |
| 4,003,841 | 1/1977 | Hachmann et al. ........ 252/186.38 X |
| 4,009,113 | 2/1977 | Green et al. .................... 252/102 X |
| 4,179,390 | 12/1979 | Spadini et al. ..................... 252/91 X |
| 4,283,301 | 8/1981 | Diehl .......................... 252/186.38 X |
| 4,290,903 | 9/1981 | MacGilp et al. ........... 252/174.13 X |
| 4,367,156 | 1/1983 | Diehl . |
| 4,412,934 | 11/1983 | Chung . |
| 4,444,674 | 4/1984 | Gray ................................ 252/91 X |

FOREIGN PATENT DOCUMENTS

| | | |
|---|---|---|
| 0006655 | 1/1980 | European Pat. Off. . |
| 2420647 | 11/1975 | Fed. Rep. of Germany . |
| 0836988 | 6/1960 | United Kingdom . |
| 0864798 | 4/1961 | United Kingdom . |
| 1420468 | 1/1976 | United Kingdom . |

OTHER PUBLICATIONS

Detergent Age (Household & Personal Products Industry), Jul., 1967, 32–FIG. 11.
Kirk–Othmer, "Organic Peroxides and Peroxy Compounds," *Encyclopedia of Chemical Technology*, 17, 60.

*Primary Examiner*—John E. Kittle
*Assistant Examiner*—Mukund J. Shah
*Attorney, Agent, or Firm*—Michael P. Brennan; Steven J. Goldstein; Jack D. Schaeffer

[57] ABSTRACT

This invention relates to peroxygen bleaching activator compounds and bleaching compositions. The peroxygen bleach activator compounds, used in combination with peroxygen bleach compounds which yield hydrogen peroxide in an aqueous solution, provide effective and efficient bleaching of textiles over a wide range of temperatures. In a highly preferred embodiment the bleaching compositions of the invention are detergent compositions.

24 Claims, No Drawings

PEROXYGEN BLEACH ACTIVATORS AND BLEACHING COMPOSITIONS

TECHNICAL FIELD

This invention relates to novel compounds and compositions useful in peroxygen bleaching. More particularly, this invention relates to novel peroxygen bleach activator compounds that aid in providing effective and efficient peroxygen bleaching of textiles over a wide range of temperatures and conditions.

This invention also relates to bleaching detergent compositions employing these peroxygen bleach activator compounds in combination with a peroxygen bleaching compound capable of yielding hydrogen peroxide in solution. In a highly preferred embodiment the bleaching compositions of the present invention are stable detergent compositions. This invention further relates to methods of making the peroxygen bleach activator compounds. Lastly, this invention relates to particularly stable bodies containing these peroxygen bleach activator compounds in combination with certain binder or enrobing compounds.

It is well known that peroxygen bleaches are effective in removing stains and/or soils, as well as visible evidence of stains and/or soils, from textiles. Unlike sodium hypochlorite bleaching solutions, they can be readily employed in a variety of bleaching and detergent compositions. However, the efficacy of peroxygen bleaches can vary greatly with temperature. These bleaches are only practicable and/or effective when the bleaching solution (bleach and water mixture) is above about 60° C. When employed in a bleach solution at a temperature of about 60° C. or below, peroxygen bleaches are significantly less efficacious than at higher temperatures. Therefore, in order to obtain a desirable level of bleaching performance at these lower temperatures, extremely high levels of peroxygen bleach must be employed. Due to the cost of peroxygen bleach compounds, levels necessary to achieve good bleaching performance at such temperatures are economically impracticable. In bleach solutions where the temperature is well below 60° C., peroxygen bleaches are rendered almost totally ineffective regardless of the level of peroxygen bleach compound added to the system.

The dependence of peroxygen bleach performance on temperature (and concentration), described above, is both practically and economically significant. Peroxygen bleaches are most commonly used as detergent adjuvants in home laundry products. Thus, the typical textile wash process employing these bleaches utilizes an automatic household washing machine and a wash-water temperature below 60° C. (The low wash-water temperature utilized reflects concern for both textile care and energy consumption.) As a consequence, there has been much interest in developing substances that would increase the efficacy of peroxygen bleach compounds allowing them to be effectively employed at a temperature below 60° C. Such substances are generally referred to in the art as bleach activators or peroxygen bleach activators.

BACKGROUND OF THE INVENTION

Numerous substances have been disclosed in the art as effective peroxygen bleach activators. Among the best known of these are the substituted and unsubstituted carboxylic acid ester bleach activators.

U.S. Pat. No. 3,130,165, Brocklehurst, issued Apr. 21, 1964, describes a household laundry detergent composition. This composition contains a detergent, from 3-20% by weight of an inorganic peroxy-compound, and from about 0.5 to about 2.5 moles of a phenol (or substituted phenol) ester of alpha-chloro-acetic or -propionic acid per mole of available oxygen.

*Detergent Age*, July, 1967, describes chloroacetyl salicylic acid as an activator for low temperature perborate/peroxide bleaching.

U.S. Pat. No. 3,075,921, Brocklehurst, et al., issued Jan. 29, 1963, discloses 2-chloro, 4-chloro, and 2-methoxy peroxybenzoic acid. These acids are described as providing excellent bleaching activity when incorporated into solid detergent compositions.

British Patent Specification No. 864,798, published Apr. 6, 1961, discloses bleaching compositions comprising an inorganic persalt combined with an organic ester of an aliphatic carboxylic acid. The addition of these esters to the wash solution is said to give a more vigorous bleaching action than the hydrogen peroxide alone. Such a system therefore permits low-temperature bleaching (50°-60° C.) under otherwise normal washing conditions. It is preferred that the ester be derived from an aliphatic carboxylic acid having not more than 10, and preferably less than 8, carbon atoms. The patentee states that such bleaching compositions are stable during storage.

British Patent Specification No. 836,988, published June 9, 1960, describes bleaching and detergent compositions containing an inorganic persalt and an organic carboxylic acid ester. It is alleged that such esters provide improved bleaching at temperatures between 50° to 60° C. when compared to systems employing the persalt alone. Specific examples include sodium dodecyl benzene sulfonate and sodium dodecyl phenyl acetate.

It is also known that bleach activators which exhibit surface activity can be used in combination with peroxygen-type bleaches to provide particularly effective surface bleaching. U.S. Pat. No. 4,283,301, Diehl, issued Aug. 11, 1981, discloses bleaching compositions comprising a peroxygen bleach, such as persalt, and a bleach activator. The activators described are esters of either an alkyl mono- or di-carboxylic acid. These activators may be represented by the general formula:

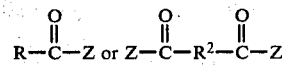

wherein R is an alkyl chain containing from about 5 to about 13 carbon atoms, $R^2$ is an alkyl chain containing from about 4 to about 24 carbon atoms, and Z is a leaving group. The patentee states that the selected bleach and bleach activator are preferably present in equimolar ratios.

U.S. Pat. No. 4,412,934, Chung, et al., discloses bleaching compositions containing a peroxygen bleaching compound and a bleach activator of the general formula:

wherein R is an alkyl group containing from about 5 to about 18 carbon atoms with the longest linear alkyl chain being from about 6 to about 10 carbon atoms; L is a leaving group. It is further required that the conjugate acid of the activator must have a pK$_a$ in the range of from about 6 to about 30. The molar ratio of the hydrogen peroxide generated:activator must be greater than about 1.5:1.

Certain benzene sulphonate compounds with an alkoxy group substituted on the ring are known to be useful in cleaning compositions. U.S. Pat. No. 3,685,127, Boldingh, et al., issued Aug. 22, 1972, describes detergent compositions with improved bleaching capability containing (1) an inorganic persalt, (2) an organic detergent and (3) a bleach precursor having the general formula:

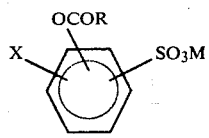

wherein X is a branched or straight chain alkyl or alkanoyl radical containing 6 to 17 carbon atoms, R is hydrogen or an alkyl radical having 1 to 7 carbon atoms, and M is an alkali metal or ammonium radical. Spray-dried detergent compositions containing 2-acetoxy-5-nonyl benzene sulfonate are disclosed.

Certain alpha-chloro and alpha-alkoxy acid esters are known to be useful as perfumes in cleaning compositions. For example, U.S. Pat. No. 3,368,943, Gilbert, issued Feb. 13, 1968, discloses compounds of the formula:

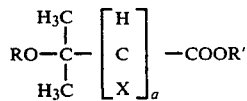

wherein a is 0 or 1; X is chlorine or bromine; R is methyl or ethyl; and R' is a saturated C$_4$–C$_{12}$ aliphatic branched or linear chain, benzyl, phenol ethyl, or phenol propyl radical. The compounds described by the patentee are said to possess an agreeable odor. These compounds include alpha-alkoxy isobutyrates and alpha-halo beta-alkoxy isovalerates. As perfumes, these compounds are said to be particularly suitable for use in detergents and "bleaching-aid" compositions. Cleaning compositions, detergent compositions, and bar soap compositions perfumed with these compounds are disclosed.

Poly-alpha-chloro acrylic acid is disclosed in the art as being useful in detergent compositions as both an oxidizing agent and as a thickener. British Patent Specification No. 1,420,468, published Jan. 7, 1976, suggests that oxidizing agents can be generated in a wash solution if the original detergent compositions contain a combination of sodium perborate and a poly-alpha-hydroxy acrylic acid, a poly-alpha-chloro acrylic acid, or a derivative of these compounds.

U.S. Pat. No. 3,553,140, McCrudden, issued May 15, 1979, discloses certain carboxyl-group-containing polymers useful as thickeners in detergent compositions which additionally contain a perborate. Alpha-chloro acrylic acid in a detergent composition is specifically disclosed.

U.S. Pat. No. 3,969,257, Murray, issued July 13, 1976, suggests that acetyl salicylic acid is useful as an activator for soluble peroxide bleaching agents in detergent compositions.

While the overall efficacy of carboxylic acid ester bleach activators most similar to those of the present invention is unquestioned, these art-disclosed compounds most similar to those of the present invention suffer from one significant drawback: they yield compounds (the active component) which possess a particularly repugnant odor under actual usage conditions (pH, temperature, etc.). Because they possess this odor under actual wash conditions, their overall utility and value is greatly reduced.

The malodor associated with these compounds (the active component) is well-known in the art. See "Organic Peroxides and Peroxy Compounds", Kirk-Othmer *Encyclopedia of Chemical Technology*, 17, 60.

U.S. Pat. No. 4,009,113, Green, et al., issued Feb. 22, 1977, discloses granular compositions comprising from about 40% to about 80% of a bleach activator and an inert carrier material such as long chain fatty acids or esters wherein said precursor is substantially evenly distributed with said precursor compound to form a composite particle. The particle has an outer protective layer which can consist of, for example, polyvinyl alcohol. It is stated that such compositions have both good storage stability and dispersibility in the wash water.

U.S. patent application Ser. No. 362,812, Gray, et al., filed Mar. 29, 1982, discloses a detergent additive composition comprising from about 75% to about 95% of a particulate infusible solid having a particle size distribution such that at least about 50% thereof passes a 250 micrometer screen and comprising storage sensitive detergent additive materials, and from about 5% to about 25% of ethoxylated nonionic surfactants melting in the range of from about 20° C. to about 60° C. wherein said composition is prepared via a radial extrusion process. It is stated that such compositions have improved storage stability together with excellent release and dispersibility characteristics in wash water.

U.S. patent application Ser. No. 433,499, Chung, filed Oct. 8, 1982, "Bodies Containing Bleach Activator", describes stable compositions employing binder and enrobing materials similar to those of the present invention. These compositions contain 4-(alkanoyloxo)benzenesulfonates.

It has now been discovered that certain alpha substituted derivatives of the C$_6$–C$_{18}$ carboxylic acid esters provide particularly effective peroxygen surface bleaching performance but do so without generating the malodor associated with the use of corresponding unsubstituted or shorter chain (art-disclosed) compounds.

It has also been discovered that these alpha substituted C$_6$–C$_{18}$ carboxylic acid esters, while very reactive, can be stabilized for storage by forming bodies containing the esters and select binder or enrobing materials, such as sorbitan esters.

It has further been discovered that these alpha substituted C$_6$–C$_{18}$ carboxylic acid esters can be simply prepared under anhydrous conditions without generating noxious products.

SUMMARY OF THE INVENTION

The present invention comprises peroxygen bleach activator compounds of the general formula

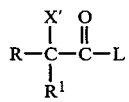

wherein R is a straight or branched alkyl or alkenyl group having from about 4 to about 14 carbon atoms, $R^1$ is H, $CH_3$, $C_2H_5$, or $C_3H_7$, X' is Cl, $OCH_3$, or $OC_2H_5$, and L is a leaving group as defined herein. The present invention also comprises bleaching and detergent compositions containing compounds of the general formula described above and a peroxygen bleaching compound capable of yielding hydrogen peroxide in an aqueous solution wherein the ratio of peroxygen bleaching compound to peroxygen bleach activator compound is about 10:1 to about 1:4.

This invention also comprises a method of making the alpha-substituted alkyl or alkenyl compounds above, where L is an oxybenzene sulfonate, comprising reacting the corresponding substituted acid chloride with the disodium salt of L under anhydrous conditions.

Further, the present invention comprises a body containing bleach activators comprising:

(a) from about 50% to about 98% of a bleach activator compound of the general formula

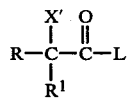

where R is a straight or branched alkyl or alkenyl group having from about 4 to about 14 carbon atoms, $R^1$ is H or $C_2H_5$, X is Cl, $OCH_3$ or $OC_2H_5$ and L is a leaving group selected from

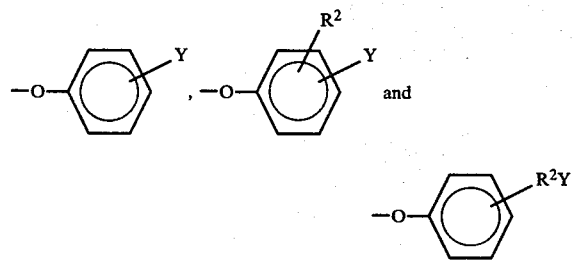

wherein $R^2$ is an alkyl chain containing from about 1 to about 8 carbon atoms, and Y is $-SO_3^-M^+$ or $COO^-M^+$ wherein $M^+$ is sodium or potassium; and (b) from about 2% to about 50% of a binder material selected from the group consisting of nonionic surfactants, polyethylene glycols, anionic surfactants, film forming polymers, fatty acids and mixtures thereof, wherein said binder does not melt below about 40° C.; and wherein (a) and (b) are substantially evenly distributed throughout said body, the density of said body is above about 1.06 g/cc and said body contains less than about 5% water. Preferred binder or enrobing materials include sorbitan monopalmitate, sorbitan monostearate, sorbitan distearate, sorbitan tristearate, or mixtures of these compounds.

DETAILED DESCRIPTION OF THE INVENTION

This invention relates to novel alpha substituted alkyl or alkenyl esters useful as peroxygen bleach activators.

These activators, when used in combination with a peroxygen bleach compound capable of yielding hydrogen peroxide in an aqueous solution, at specific molar ratios of available hydrogen peroxide in solution to activator, provide extremely effective and efficient bleaching of stains from textiles. Such compositions remove stains and/or soils from textiles, as well as the visible evidence of stains and/or soils. The bleaching activity of these compositions makes them particularly effective in the removal of dingy soils. Dingy soils are frequently a blend of particulate and greasy materials that build up on textiles after numerous washings; these soils give white textiles a gray tint. Removing soils of this type is sometimes referred to in the art as "dingy fabric clean-up".

The bleaching compositions employing the activators of the present invention provide this effective bleaching over a wide range of temperatures. Without the bleach activator compounds of the present invention, such peroxygen bleaching compounds would be ineffective and/or impractical at temperatures below about 60° C. The improved bleaching activity obtained by employing the activators of the present invention is observed when the bleach solution temperature is at least about 5° C.

Compounds similar to those of the present invention which are known in the art can be logically separated into two classes. The first class of known compounds are the corresponding unsubstituted compounds, compounds with similar or identical chain lengths and leaving groups but without the chlorine, methoxy or ethoxy group substituted at the alpha (2) position. The second class of known compounds are compounds with the chlorine, methoxy or ethoxy substitution but possessing a chain length (the alkyl or alkenyl chain with the substitution) of only 2–3 carbon atoms. The activators most similar to those of the instant invention from both of these classes of compounds suffer from the same disadvantage: they yield compounds (the active component or species) which possess an offensive, unpleasant odor under actual usage conditions (pH, temperature, etc.). This characteristic malodor makes the use of either class of known compounds undesirable for two reasons. First, this odor is detectable when the compounds are placed in solution, i.e. during use. Second, the malodor associated with these compounds lingers, remaining on any textile or fabric which has been placed in a bleaching solution containing them. Thus, the malodor is noticeable both during and after use.

The compounds of the present invention, particularly the alpha chloro substituted compounds, possess two significant advantages over the art-disclosed compounds discussed above. Most importantly, they do not generate, either during or after use, the malodor which is characteristic of the use of the art-disclosed compounds. Secondly, under common usage conditions, the compounds of the present invention are frequently capable of providing equivalent peroxygen bleaching while employing lower levels of peroxygen bleaching compound than would be required for the art-disclosed compounds. In this context they are more efficient.

Peroxygen Bleach Activators

The present invention comprises peroxygen bleach activator compounds of the general formula

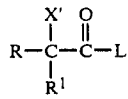  (I)

wherein R is a branched or linear alkyl or alkenyl group having from about 4 to about 14 carbon atoms; $R^1$ is H, $CH_3$, $C_2H_5$ or $C_3H_7$; X' is Cl, $OCH_3$ or $OC_2H_5$; and L is a leaving group the conjugate acid of which has a $pK_a$ in the range of from about 4 to about 30. These compounds, when used in combination with a peroxygen bleaching compound capable of yielding hydrogen peroxide in an aqueous solution, provide particularly effective peroxygen bleaching over a wide range of temperatures and conditions.

L in the above formula can be essentially any useful leaving group. A leaving group is any group that is displaced from the bleach activator in a peroxygen bleaching solution as a consequence of the nucleophilic attack on the bleach activator by the perhydroxide anion. This perhydrolysis reaction results in the formation of a percarboxylic acid. Generally, for any group to be useful as a leaving group in the compounds and compositions of the present invention, it must exert an electron attraction or an "electron attracting effect". This facilitates the formation of the peroxy acid anion. Leaving groups that exhibit this behavior are those with a corresponding conjugate acid that has a $pK_a$ in the range of from about 4 to about 30, preferably about 4 to 16, more preferably about 6 to about 13, and even more preferably from about 7 to about 11. If sustained bleaching activity over a long period of time is desired, then employing groups with $pK_a$ values other than those indicated as preferred (different perhydrolysis rates), or mixtures of groups having various $pK_a$ values, may be desirable.

Preferred bleach activator compounds of the present invention are those of the above general formula (I) wherein R, $R^1$ and X' are as defined in the general formula (I) and L is selected from the group consisting of:

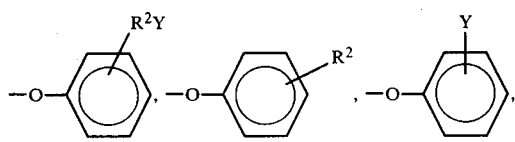

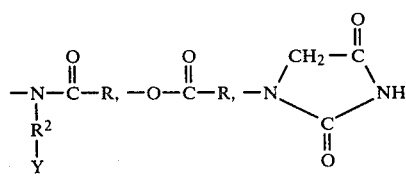

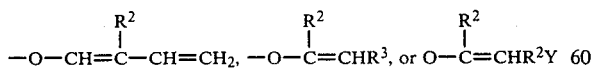

wherein $R^2$ is an alkyl chain containing from about 1 to about 8 carbon atoms, $R^3$ is H or an alkyl chain containing from about 1 to about 8 carbon atoms, and Y is H or a group which provides solubility (as defined herein) to the bleach activator compounds of the present invention in water at 5° C. or 45° C., hereinafter referred to as "a solubilizing group". The preferred solubilizing groups are $—SO_3^-M^+$, $—COO^-M^+$, $—SO_4^-M^+$, $(—N^+R_3^4)X^-$ and $O \leftarrow NR_2^4$, and most preferably $—SO_3^-M^+$ and $—COO^-M^+$, wherein $R^4$ is an alkyl chain containing from about 1 to about 4 carbon atoms, M is a cation which, when combined with X, provides solubility to the bleach activator compounds of the present invention. Preferably, M is an alkali metal, ammonium or substituted ammonium cation, with sodium and potassium being most preferred, and X is a halide, hydroxide, methylsulfate or acetate anion. It should be noted that bleach activator compounds of the present invention which possess a leaving group that does not contain a solubilizing group should be well dispersed when employed in a bleaching solution in order to assist in their dissolution. By providing solubility, as used herein, is meant that the group or groups selected make the final bleach activator compound sufficiently soluble to provide a concentration at least 3 parts per million of activator in the bleach solution at either 5° C. or 45° C., or at both temperatures.

Alpha substituted (Cl, or $OCH_3$ or $OC_2H_5$) alkyl or alkenyl carboxylic acid diol, polyol, and sugar esters are also useful. Preferred sugar ester bleach activator compounds of the present invention include glucose, sucrose, and lactose esters of the formula

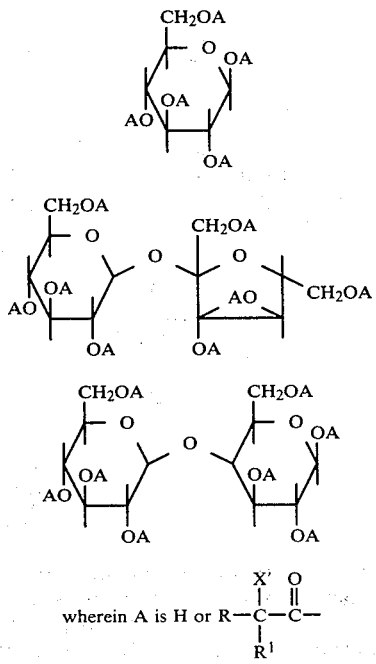

wherein A is H or $R—\overset{X'}{\underset{R^1}{C}}—\overset{O}{C}—$ wherein R is a branched or linear alkyl or alkenyl group having from about 4 to about 14 carbon atoms; $R^1$ is H, $CH_3$, $C_2H_5$ or $C_3H_7$; and X' is Cl, $OCH_3$ or $OC_2H_5$; provided that at least one A is not H. In preferred sugar ester peroxygen bleach activator compounds of the present invention, no A is H.

Preferred bleach activator compounds of the present invention are also those of the above general formula (I) wherein L, X' and $R^1$ are as defined in the general formula (I) and R is a branched or linear, and preferably linear, alkyl group containing from about 4 to about 10 carbon atoms. Those having a linear alkyl R group containing from about 6 to about 10 are more preferred. Even more preferred are bleach activator compounds of the present invention of the above general formula (I) wherein L is as defined in the general formula and R is a linear alkyl chain containing from about 6 to about 8 carbon atoms.

Preferred bleach activator compounds of the present invention are those of the above general formula (I) wherein R and L are as defined above, and $R^1$ is H or $C_2H_5$, with $R^1$ as H particularly preferred.

Thus, the preferred bleach activator compounds of the present invention are those of the above general formula (I) wherein R is a linear alkyl chain containing from about 6 to about 10, and more preferably from about 6 to about 8 carbon atoms, $R^1$ is H or $C_2H_5$, and preferably H, X' is Cl, and L is selected from the group consisting of:

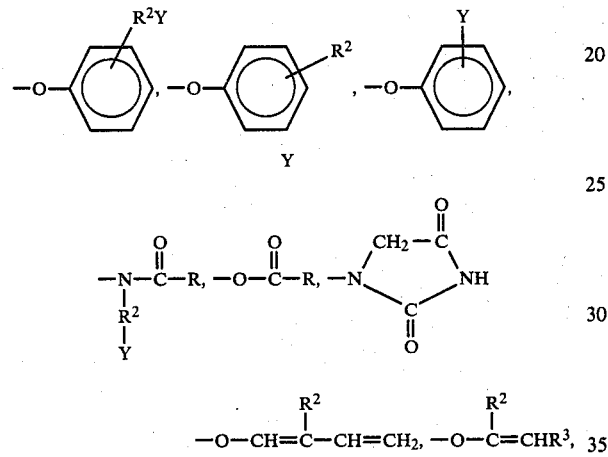

wherein R, $R^2$, $R^3$ and Y are as defined above.

More preferably, the bleach activator compounds of the present invention are those of the above general formula (I) wherein R is a linear alkyl group containing from about 6 to about 10 carbon atoms, X' is Cl, $R^1$ is H or $C_2H_5$, preferably H, and L is selected from the group consisting of:

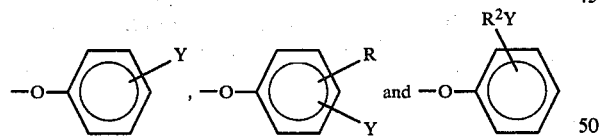

wherein $R^2$ is as defined above and Y is $-SO_3^-M^+$ or $-COO^-M^+$ wherein M is as defined above.

Preferred branched alkyl chain bleach activator compounds of the present invention are those of the above general formula (I) wherein R is a branched alkyl chain containing from about 6 to about 12 carbon atoms wherein the longest linear alkyl portion of said chain contains from about 4 to about 10 carbon atoms, X' is Cl, $R^1$ is H or $C_2H_5$, and L is selected from the group consisting of

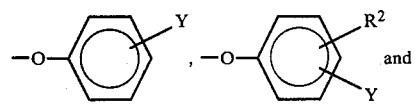

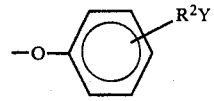

wherein $R^2$ is an alkyl chain containing from about 1 to about 8 carbon atoms, Y is $-SO_3^-M^+$ or $-COO^-M^+$ wherein M is sodium or potassium.

Highly preferred bleach activator compounds of the present invention are those of the above general formula (I) wherein R is a linear alkyl chain containing from about 6 to about 10, and preferably from about 6 to about 8 carbon atoms, $R^1$ is H or $C_2H_5$, and preferably H, X is Cl and L is selected from the group consisting of:

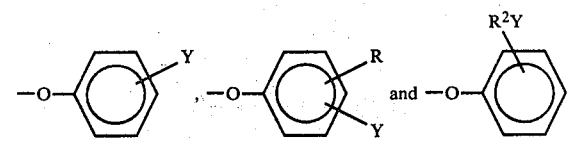

wherein $R^2$ is as defined above and Y is $-SO_3^-M^+$ or $-COO^-M^+$ wherein M is as defined above.

The most highly preferred bleach activator compounds of the present invention are of the formula:

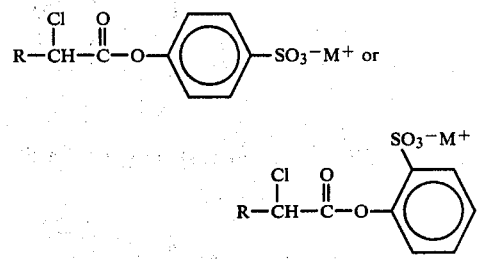

wherein R is a linear alkyl chain containing from about 6 to about 10, and preferably from about 6 to about 8, carbon atoms, and M is sodium or potassium.

Representative peroxygen bleach activator compounds of the present invention include, without limitation,

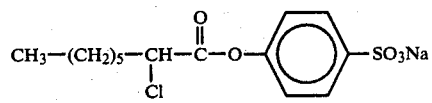

Sodium 4-(2-chlorooctanoyloxy)benzenesulfonate;

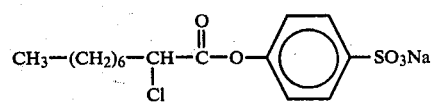

Sodium 4-(2-chlorononanoyloxy)benzenesulfonate;

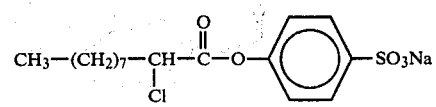

Sodium 4-(2-chlorodecanoyloxy)benzenesulfonate;

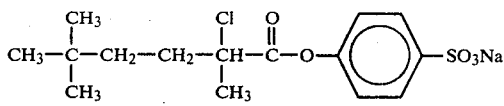

Sodium 4-(3,5,5-trimethyl-2-chlorohexanoyloxy)benzene sulfonate;

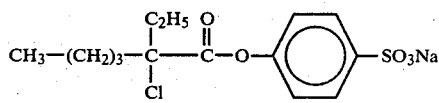

Sodium 4-(2-chloro-2-ethyl-hexanoyloxy)benzenesulfonate;

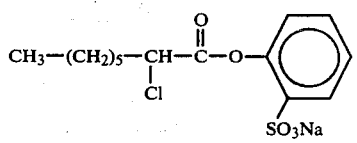

Sodium 2-(2-chlorooctanoyloxy)benzenesulfonate

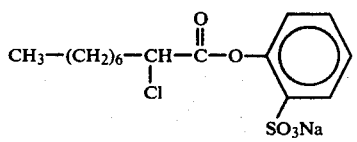

Sodium 2-(2-chlorononanoyloxy)benzenesulfonate

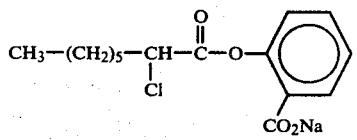

Sodium 2-(2-chlorooctanoyloxy)benzoate

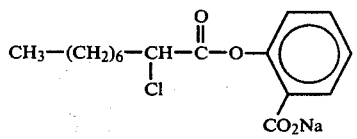

Sodium 2-(2-chlorononanoyloxy)benzoate

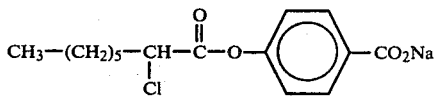

Sodium 4-(2-chlorooctanoyloxy)benzoate and

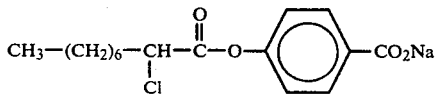

Sodium 4-(2-chlorononanoyloxy)benzoate

The Peroxygen Bleaching Composition

The present invention also comprises bleaching and detergent compositions containing compounds of the general formula (I) described above and a peroxygen bleach compound capable of yielding hydrogen peroxide in an aqueous solution wherein the ratio of peroxygen bleach compound to peroxygen bleach activator compound is about 10:1 to about 1:4, by weight of the composition. Ratios of about 3:1 to about 1:2 are preferred, with ratios of about 3:1 to about 1:1, by weight of the composition, particularly preferred.

The preferred molar ratio of available hydrogen peroxide generated in solution (the bleaching solution or liquor) by the peroxygen bleach compound to bleach activator compound is about 3:1 to about 1:3. It should be noted that such a ratio can also generally be expressed as the molar ratio of peroxygen bleach compound to peroxygen bleach activator because the vast majority of peroxygen bleach compounds theoretically yield one mole of hydrogen peroxide (in solution) per mole of peroxgen bleach compound.

It will be appreciated by examining the preferred ratios (of peroxygen bleach compound to peroxygen bleach activator compound) described above, that the bleaching compositions of the present invention possess a second significant advantage over many very similar art-disclosed compounds; they are extremely efficient. Much lower levels of the peroxygen bleach activator compounds of the present invention are required (on a molar basis) to achieve bleaching performance equivalent to that of many very similar art-disclosed compounds.

The peroxygen bleach activators of the present invention are particularly useful in peroxygen bleaching compositions designed for the surface bleaching of fabrics or textiles, especially dingy soil clean-up. The peroxygen bleaching compounds useful herein, i.e., in combination with one or more of the peroxygen bleach activators of the present invention, are those capable of yielding hydrogen peroxide in an aqueous solution. These compounds are well known in the art and include hydrogen peroxide; the alkali metal peroxides; organic peroxide bleaching compounds such as urea peroxide; and inorganic persalt bleaching compounds, such as the alkali metal perborates, percarbonates, perphosphates, and the like. Mixtures of two or more such bleaching compounds, or mixtures of two or more activator compounds, can also be used, if desired.

Preferred peroxygen bleach activator compounds of the present invention for use in bleaching compositions include sodium 4-(2-chlorooctanoyloxy)benzenesulfonate; sodium 4-(2-chlorononanoyloxy)benzenesulfonate; sodium 4-(2-chlorodecanoyloxy)benzenesulfonate; sodium 4-(3,5,5-trimethyl-2-chlorohexanoyloxy)benzenesulfonate; sodium 4-(2-chloro-2-ethylhexanoyloxy)benzenesulfonate; sodium 2-(2-chlorooctanoyloxy)benzenesulfonate; sodium 2-(2-chlorononanoyloxy)benzenesulfonate; and sodium 2-(2-chlorodecanoyloxy)benzenesulfonate; sodium 4-(2-chlorononanoyloxy)benzenesulfonate; sodium 4-(2-chlorodecanoyloxy)benzenesulfonate; and sodium 4-(2-chlorodecanoyloxy)benzenesulfonate.

Preferred peroxygen bleaching compounds include sodium perborate, commercially available in the form of mono- and tetrahydrates, sodium carbonate peroxyhydrate, sodium pyrophosphate peroxyhydrate, urea peroxyhydrate, and sodium peroxide. More preferably, the peroxygen bleaching compound is selected from the group consisting of sodium perborate monohydrate, sodium perborate tetrahydrate, and sodium carbonate peroxyhydrate. Particularly preferred are sodium perborate tetrahydrate and sodium perborate monohydrate. Sodium perborate monohydrate is especially preferred because it is stable during storage yet dissolves very quickly in the bleaching solution. It is believed that such rapid dissolution results in the formation of higher levels of percarboxylic acid and, thus, enhances surface bleaching performance.

Useful levels of peroxygen bleach compound within the bleaching compositions of the invention are from about 0.1% to about 95%, and preferably from about 1% to about 60%, by weight of the bleaching composition, preferably utilizing the ratios described above. When the bleaching compositions within the invention are also detergent compositions it is preferred that the level of peroxygen bleach is from about 1% to about 20%, by weight of the detergent composition, preferably utilizing the peroxygen bleach compound:peroxygen bleach activator weight ratios described above.

The level of bleach activator compound within the compositions of the invention is from about 0.1% to about 60%, and preferably from about 0.5% to about 40%, more preferably about 0.5% to about 20%, by weight of the bleaching composition, preferably utilizing the peroxygen bleach compound:peroxygen bleach activator weight ratios described above. When the bleaching compositions within the invention are also detergent compositions it is preferred that the level of bleach activator is from about 0.5% to about 20%, and more preferably about 5% to about 20% by weight of the detergent composition, preferably utilizing the peroxygen bleach compound:peroxygen bleach activator weight ratios described above.

Mixtures of the bleach activator compounds of the present invention and other conventional peroxygen bleach activator compounds may also be employed. For example, mixtures of the compounds of the present invention and the peroxygen bleach activators described in U.S. Pat. No. 3,130,165, Brocklehurst, issued Apr. 21, 1964; British Patent Specification No. 864,798, published Apr. 6, 1961; British Patent Specification No. 836,988, published June 9, 1960; U.S. Pat. No. 4,283,301, Diehl, issued Aug. 11, 1981; U.S. Pat. No. 3,075,921, Brocklehurst, et al., issued Jan. 29, 1963; U.S. Pat. No. 4,412,934, Chung, et al., issued Nov. 1, 1983; and U.S. Pat. No. 3,936,537, Baskerville, et al., issued Feb. 3, 1976; all incorporated herein by reference may be employed. Preferred peroxygen bleach activators for use in combination with the compounds of the present invention in the bleaching compositions of the present invention include sodium 4-octanoyloxybenzenesulfonate, sodium 4-nonanoyloxybenzene, tetra acetyl ethylene diamine, tetra acetyl methylene diamine, and tetra acetyl glycouril at a level of total activator of about 0.5% to about 40%, and more preferably about 0.5% to about 20%, by weight of the composition. When such mixtures are used in bleaching compositions which are detergent compositions, the level of total activator is preferably about 0.5% to about 20%. A molar ratio of total available hydrogen peroxide generated in solution by the peroxygen bleach compound to total peroxygen bleach activator in compositions employing such a mixture of about 3:1 to about 1:2 by weight is preferred. The ratio of activator compound of the present invention to conventional bleach activator is preferably about 1:3 to about 3:1.

The bleaching compositions of the present invention, including detergent compositions, are preferably employed at a pH (i.e., bleaching or detergent solution or liquor) of about 8 to about 11, with a pH of about 8.5 to about 10.5 preferred.

BLEACH BODIES

The character of peroxygen bleach activator compounds can be significantly altered during storage. (See U.S. Pat. No. 4,412,934, Chung, et. al., issued Nov. 1, 1983.) This is particularly true of the bleach activator compounds of the present invention. If stored as part of a bleaching or detergent composition, the peroxygen bleach activators of the present invention may interact with other bleaching (e.g., perborate) or detergent components. They may also react with the moisture inherently present in either type of composition, or with the moisture in the environment in which they are stored. The bleach activator compounds of the present invention must therefore be protected from the environment during storage to retain efficacy. However, it is critical that the selected method of protecting the bleach activator compounds of the present invention from their environment (especially moisture) during storage not substantially inhibit their ability to disperse in water.

This invention relates to a body containing stabilized, particulate peroxygen bleach activators which comprises specific bleach activators and binder or enrobing materials, both of which are defined herein. The peroxygen bleach activators incorporated in the body have excellent storage stability (are well protected from their environment) and yet readily disperse and release in water. Also, when the bodies are formed in the practice of the present invention, a superior level of bleaching performance on textiles is obtained.

It is preferred that the peroxygen bleach activator and binder or enrobing material are substantially evenly distributed throughout the body. The body must also have the proper density. Compacting the bleach activator compound particles to form a body with a density within the invention and then coating it with the binder material may not provide the maximum level of storage stability. Only when the bleach activator and binder material are substantially evenly distributed throughout the body is the storage stability maximized. However, it is also essential that the density of the body be above about 1.06 grams/cubic centimeter (g/cc), preferably above about 1.08 g/cc, most preferably from about 1.10 g/cc to about 1.30 g/cc. When the peroxygen bleach activator and binder or enrobing material are substantially evenly distributed throughout the body, densities below about 1.06 g/cc may not provide the desired level of storage stability.

Specific densities may be measured by a mercury displacement method, described as follows. Air is removed from a vessel containing a weighed sample of the particles (bodies), mercury is introduced, and the pressure increased in increments. The rate of volume decrease (or density increase) is typically one value when interparticulate spaces are being filled, which occurs first, and a different value when the voids in the particle are being filled. The inflection point on the volume-pressure curve is taken as indicating the specific density of the particles.

To achieve maximum storage stability, the body should also be essentially free of moisture. The presence of excess free moisture will result in very poor storage stability because of the peroxygen bleach activator's susceptability to hydrolysis. Thus, preferred bodies contain less than about 5% water, more preferably less than 3% water, and most preferably less than about 1.5% water, by weight of the body.

Control of the particle size of the body is also of some importance for obtaining optimum storage stability and dispersibility in the wash water. It is preferred that the bodies of the present invention, when employed in a bleaching or detergent composition, have a particle size distribution of from about 50 microns to about 2.5 millimeters wherein no more than about 5% of the bodies are greater than about 2 millimeters. More preferably, the bodies of the present invention, when employed in a bleaching or detergent composition, have a particle size distribution of from about 300 microns to about 1.5 millimeters.

The body can be made by essentially any apparatus that is suitable to substantially evenly distribute the bleach activator and binder material throughout the body and compact the body in order to obtain the required density. For example, powder blenders can be utilized to mix the bleach activator and binder material and then the mixture can be passed through a radial or axial extruder. A compaction press may also be employed to form the body. Radial or axial extruders are preferred because it is believed that they produce a body in which the bleach activator has both superior storage stability and dispersibility in the wash water. When the bleach activator and binder material are mixed, the binder material is preferably in fluid form. This can be accomplished by heating the mixture until the binder material melts. When employing binder materials that decompose rather than melt upon heating, an aqueous solution can be formed.

The following is a detailed description of the essential components of the body containing the peroxygen bleach activators of the present invention. All percentages, parts and ratios are by weight of the body unless otherwise indicated.

The level of bleach activator useful within the bodies of the present invention is from about 50% to about 99.5%, preferably about 50% to about 98%, and more preferably from about 85% to about 96%, by weight of the body.

Bleaching compositions employing the bodies of the present invention comprise from about 0.1% to about 60%, and preferably about 0.5% to about 40%, by weight of the composition of the bodies of the present invention, and from about 0.1% to about 95%, preferably about 1% to about 60%, by weight of the composition, of a peroxygen bleaching compound capable of yielding hydrogen peroxide in an aqueous solution. When these bleaching compositions are also detergent compositions, it is preferred that the level of bleach bodies is from about 0.5% to about 20%, by weight of the detergent composition, and that the level of peroxygen bleaching compound is from about 1% to about 20%, by weight of the detergent composition, and that the composition further comprises about 1% to about 30% of a detergent surfactant. Preferred ratios of bodies:peroxygen bleaching compound are the same as those described herein for activator alone to peroxygen bleaching compound.

It is also preferred that the bleach activator particle size distribution within the bleaching or detergent composition is from about 5 microns to about 2.5 millimeters. More preferably, no more than about 2% of the particles are greater than about 2 millimeters. Most preferably, the particle size distribution is from about 25 microns to about 150 microns.

The Binder or Enrobing Materials

The materials that can be utilized as binders or enrobing materials are the nonionic surfactants, polyethylene glycols, fatty acids, anionic surfactants, film forming polymers and mixtures of these materials. It is believed that such binder or enrobing materials are not reactive with the bleach activators of the present invention. If the body is placed in a detergent composition, the binder or enrobing material should not be reactive with the components of the detergent composition upon storage. Ideal binder or enrobing materials have a low hygroscopicity upon storage but should be soluble or dispersable in water. This allows for dispersion and release of the peroxygen bleach activator in the bleach or wash solution. It is also essential that the employed binder or enrobing materials do not melt below about 40° C. The binder would likely melt upon storage; frequently the storage temperature for such compositions is as high as 40° C. Any melting of the binder or enrobing material results in the bleach activator being quite unstable. (While some of the binder materials within the invention will decompose rather than melt upon exposure to of heat, the temperature at which such binder materials decompose is well beyond any temperature at which the bodies will likely be stored.)

Examples of other nonionic surfactants that can be utilized as binder or enrobing materials are the condensation products of primary or secondary aliphatic alcohols having from 8 to 24, and preferably about 9 to about 18, carbon atoms, in either a straight or branched chain configuration, with from about 35 to about 100 moles, and preferably about 40 to about 80 moles, of ethylene oxide per mole of alcohol. The preferred nonionic surfactants are prepared from primary alcohols which possess either linear (such as those derived from natural fats, or prepared by the Ziegler process from ethylene, e.g., myristyl, cetyl, and stearyl alchols), or partly branched carbon chains (such as the Dobanols and Neodols which have about 25% 2-methyl branching, Dobanol and Neodol being Trade Names of Shell; Synperonics, which are understood to have about 50% 2-methyl branching, Synperonic being a Trade Name of I.C.I.; or the primary alcohols having more than 50% branched chain structure sold under the Trade Name Lial, by Liquichimica).

Other suitable nonionic surfactants are the polyethylene oxide condensates of alkyl phenols. These include the condensation products of alkyl phenols having an alkyl group containing from 6 to 12 carbon atoms, in either a straight or branched chain configuration, with ethylene oxide. The ethylene oxide is preferably present in amounts equal to about 35 to about 100, more preferably about 40 to about 80, moles of ethylene oxide per mole of alkyl phenol. The alkyl substituent in such compounds may be derived, for example, from polymerised propylene, di-isobutylene, octene and nonene.

Nonionic surfactants suitable for use herein also include the compounds formed by condensing ethylene oxide with a hydrophobic base. The hydrophobic base is formed by the condensation of propylene oxide with propylene glycol. The molecular weight of the hydrophobic portion generally falls in the range of about 1500 to 1800. Such synthetic nonionic detergents are items of commerce. They are available from Wyandotte Chemicals Corporation as "Pluronics".

Suitable polyethylene glycols are homopolymers of ethylene oxide having the general formula $$HO(C_2H_4O)_nH,$$

have an average molecular weight of from about 2,000 to about 15,000, preferably from about 3,000 to about 10,000 and most preferably from about 4,000 to about 8,000.

The fatty acids suitable for use in the bodies of the present invention include the higher fatty acids containing from about 8 to about 24, and preferably from about 12 to about 18, carbon atoms. It has also been observed that mixtures of fatty acids and nonionic binder materials, e.g., polyethylene glycols or nonionic surfactants, provide the bleach activator with particularly good storage stability and dispersibility in the wash water. It is believed that fatty acids reduce the hygroscopicity of the nonionic binder materials and that the nonionic binder materials improve the dispersibility of the fatty acids. pH of the body can also be controlled with such materials when this is important.

Suitable anionic surfactants useful as binder or enrobing materials in the bodies of the present invention include the water-soluble salts, preferably the alkali metal, ammonium and alkylolammonium salts, of organic sulfuric reaction products having in their molecular structure an alkyl group containing from about 8 to about 20 carbon atoms and a sulfonic or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms), and the sodium and potassium alkylbenzene sulfonates in which the alkyl group contains from about 9 to about 15 carbon atoms in a straight or branched chain configuration. These are described in U.S. Pat. Nos. 2,220,099 and 2,477,383, both incorporated herein by reference. The preferred anionic surfactants are linear straight chain alkylbenzene sulfonates in which the average number of carbon atoms in the alkyl group is from about 11 to 13, abbreviated as $C_{11-13}$LAS.

Other anionic surfactants useful as binder or enrobing materials in the bodies of the present invention are the water-soluble salts of the higher fatty acids or "soaps". This includes alkali metal soaps such as the sodium, potassium, ammonium, and alkylolammonium salts of the higher fatty acids containing from about 8 to about 24, and preferably from about 12 to about 18, carbon atoms. Soaps can be made by direct saponification of fats and oils or by the neutralization of free fatty acids.

Anionic surfactants useful as binder or enrobing materials in the bodies of the present invention also include the the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule or unit and wherein the alkyl groups contain from about 8 to about 12 carbon atoms; and the sodium or potassium salts of alkyl ethylene oxide ether sulfates containing about 1 to about 10 units of ethylene oxide per molecule or unit and wherein the alkyl group contains from about 10 to about 20 carbon atoms.

Still other anionic surfactants useful as binder or enrobing materials in the bodies of the present invention include the water-soluble salts of the esters of alpha-sulfonated fatty acids containing from about 6 to about 20 carbon atoms in the fatty acid group and from about 1 to about 10 carbon atoms in the ester group; the water-soluble salts of 2-acyloxyalkane-1-sulfonic acids containing from about 2 to about 9 carbon atoms on the acyl group and from about 9 to about 23 carbon atoms in the alkane moiety; the water-soluble salts of olefin and paraffin, sulfonates containing from about 12 to about 20 carbon atoms; and beta-alkyloxy alkane sulfonates containing from about 1 to about 3 carbon atoms in the alkyl group and from about 8 to about 20 carbon atoms in the alkane moiety.

Suitable film forming polymers useful as binder or enrobing materials in the bodies of the present invention are the polymers derived from the monomers such as vinyl chloride, vinyl alcohol, furan, acrylonitrile, vinyl acetate, methyl acrylate, methyl methacrylate, styrene, vinyl methyl ether, vinyl ethyl ether, vinyl propyl ether, acrylamide, ethylene, propylene and 3-butenoic acid.

Preferred polymers of the above group are the homopolymers and copolymers of acrylic acid, hydroxyacrylic acid, or methacrylic acid, which in the case of the copolymers contain at least about 50%, and preferably at least about 80%, by weight, units derived from the acid. The particularly preferred polymer is sodium polyacrylate. Other specific preferred polymers are the homopolymers and copolymers of maleic anhydride, especially the copolymers with ethylene, styrene and vinyl methyl ether. These polymers are commercially available under the trade names Versicol and Gantrez.

Other film-forming polymers useful as binder or enrobing materials in the bodies of the present invention include the cellulose sulfate esters such as cellulose acetate sulfate, cellulose sulfate, hydroxyethyl cellulose sulfate, methylcellulose sulfate and hydroxypropylcellulose sulfate.

Surprisingly, very small levels of binder or enrobing material within the body are required. The level of binder material useful within the bodies within the invention is from about 0.5% to about 50%, preferably from about 2% to about 50%, and more preferably from about 4% to about 15% by weight of the body.

Examples of preferred binder or enrobing materials include the fatty acid esters of alcohols, diols and polyols. For example, sorbitan fatty acid esters selected from the group sorbitan, monolaurate, dilaurate, trilaurate, monopalmitate, monostearate, distearate, tristearate, monooleate, dioleate, and trioleate, are preferred. These materials are items of commerce and are known as "Spans", a Trade Name of the I.C.I. Americas, Inc. Ethoxylated varieties of these compounds are also useful. For example, sorbitan esters having an average total level of ethoxylation of from about 4 to about 100, and preferably about 20 to about 85 moles of ethylene oxide per mole of sorbitan, are preferred.

Particularly preferred binder materials include sorbitan monopalmitate, sorbitan monostearate, sorbitan distearate, and sorbitan tristearate. Polyethylene glycols having an average molecular weight of from about 4,000 to about 8,000 are also useful and preferred. A mixture of lauric acid:PEG 8000, in a weight:weight ratio of about 2:1 to about 1:2, more preferably about 1:1, is also preferred.

The binder or enrobing material need not be completely inert; the binder or enrobing material can be selected to benefit the overall bleaching activity of the system. For example, employing 14%, by weight of a body, of $C_{13}LAS$ as the binder for the peroxygen bleach activator 4-(2-chlorodecanoyloxo)benzenesulfonate can significantly increase the rate of solubility of the peroxygen bleach activator.

The bodies of the present invention may also contain all of the usual components of detergent compositions including the ingredients set forth in U.S. Pat. No. 3,963,537, Baskerville et al., incorporated herein by reference, so long as they are inert with respect to the bleach activator and binder material. Such components include other peroxygen bleach activators, color speckles, suds boosters, suds suppressors, antitarnish and/or anticorrosion agents, soil-suspending agents, soil-release agents, dyes, fillers, optical brighteners, germicides, alkalinity sources, hydrotropes, antioxidants, enzymes, enzyme stabilizing agents, perfumes, etc.

In a highly preferred embodiment, the bodies of the present invention comprise (a) from about 85% to about 96% of a peroxygen bleach activator compound having the general formula

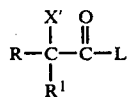

wherein R is a straight or branched chain alkyl or alkenyl having from about 4 to about 14 carbon atoms; $R^1$ is H or $C_2H_5$, X' is Cl, and L is selected from the group consisting of $O-O-SO_3^-M^+$ and $O-O-CO_2^-M^+$ wherein M is sodium or potassium; and (b) about 4% to about 15% of a binder material selected from the group consisting of sorbitan fatty acid esters, ethoxylated varieties of these sorbitan esters having an average total level of ethoxylation of from about 4 to about 8 moles of ethylene oxide per mole of sorbitan; linear alkylbenzenesulfonates in which the average number of carbon atoms in the alkene moiety is about 11 to about 13; aliphatic alcohols containing between 9 and 18 carbon atoms ethoxylated with between 40 and 80 moles of ethylene oxide; sodium polyacrylate; polyethylene glycols having a molecular weight of from about 4000 to about 8000, fatty acids containing from about 12 to about 18 carbon atoms; and mixtures thereof; the density of said body is from about 1.10 g/cc to about 1.30 g/cc, said body contains less than about 1.5% water and said body has an average particle size distribution of from about 300 microns to about 1.5 millimeters.

REACTION METHOD

In accordance with the reaction method of the present invention, the alpha substituted alkylphenylsulfonates are prepared by contacting the corresponding alpha-substituted acid chloride with disodium phenolsulfonate under anhydrous conditions. A representation of this reaction is as follows:

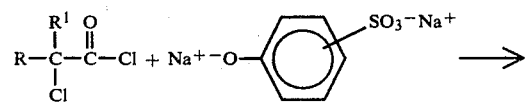

-continued

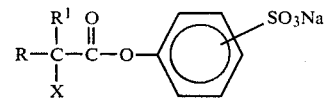

wherein R is a straight or branched chain alkyl or alkenyl having from about 2 to about 20 carbon atoms, X is H, Cl, $OCH_3$ or $OC_2H_5$, and $R^1$ is H or $C_2H_5$. Preferred acid chlorides for use in the methods of the present invention are those of the above general reaction formula wherein R is about 4 to about 12 carbon atoms, and more preferably about 6 to about 8 carbon atoms. Accordingly, the present process is particularly useful for preparing sodium 4-(2-chlorooctanoyloxy)benzenesulfonate; sodium 4-(2-chlorononanoyloxy)benzenesulfonate; sodium 4-(2-chlorodecanoyloxy)benzenesulfonate; sodium 4-(3,5,5-trimethyl-2-chlorohexanoyloxy)benzenesulfonate; sodium 4-(2-chloro-2-ethylhexanoyloxy)benzenesulfonate; sodium 2-(2-chlorooctanoyloxy)benzenesulfonate; sodium 2-(2-chlorononanoyloxy)benzenesulfonate; and sodium 2-(2-chlorodecanoyloxy)benzensulfonate.

Both of the starting components necesssary for the method of the present invention can be prepared by conventional means. The acid chloride starting component may be prepared by conventional methods, or by the regiospecific methods described in U.S. Pat. No. 4,148,811, Crawford, issued Apr. 10, 1979; or U.S. Pat. No. 4,368,140, Crawford, issued Jan. 11, 1983; both incorporated herein by reference. The alpha-substituted carboxylic acid may also be prepared employing the carboxylic acid, chlorine, a second strong acid, a free radical inhibitor and an organic acid anhydride as described in Example VI of the present specification. The alpha substituted carboxylic acid can then be converted by conventional means, such as reacting the carboxylic acid with $SOCl_2$, $PCl_3$ or $PCl_5$, and the like, to obtain the acid chloride. The second starting component, the disodium phenylsulfonate, can also be prepared by conventional means. As represented in Example IV, the monosodium salt can be put into solution, an equivalent molar quantity of sodium hydroxide is added, and the water removed.

The present process is not limited with regard to the method of preparing either of the starting components. The method employed to prepare either the acid chloride or the disodium phenolsulfonate plays no part in the practice of the present invention. For example, an unsubstituted acid chloride may be converted to an alpha-substituted acid chloride according to Example II, column 7, lines 5-11 of U.S. Pat. No. 4,368,140, discussed above. The acid chloride so prepared can then be used as a starting component in the reaction of the present invention.

The process reaction herein can be carried out in the presence or absence of inert solvents. For example, monoglyme, diglyme, toluene, and the like, are good solvents for this reaction. Other useful solvents include dioxane, xylene, chlorobenzene, tetrahydrofuran and t-butyl-methylether. Preferably, the reaction is carried out with the use of monoglyme or diglyme. These solvents are particularly useful due to their boiling point, with monoglyme most preferred. The reaction is carried out under anhydrous conditions. By anhydrous conditions, as used herein, is meant that reaction environment or solvent is sufficiently free of water so that no side reactions take place. Preferably, any solvent employed contains less than about 5%, more preferably less than about 1%, and most preferably less than about 0.5%, water, by weight of solvent.

The reaction process of this invention is exothermic. Accordingly, the rate at which this reaction will proceed may be easily controlled by controlling the rate at which the heat is allowed to dissipate from the reaction environment. Because the heat from such a reaction is generally conducted away via any solvent employed, selecting a solvent such as monoglyme with a boiling point (760) of about 82°–83° C. allows the reaction temperature to be controlled by solvent. Under such conditions, the reflux takes place at the boiling point of the solvent and the temperature is controlled accordingly. In turn, the rate of the reaction is also controlled.

While it is desirable to control the temperature of the reaction with a solvent, it is not necessary to do so. The reaction method of the present invention may be conducted and maintained at any temperature which is high enough to allow the reaction to begin, but low enough to prevent decomposition of the desired product. Reactions of the present invention have reached temperatures of about 277° C. with no significant disadvantages becoming apparent. However, it is preferred that the reaction methods of the present invention be commenced and maintained at about 15° C. to about 150° C., more preferably about 15° C. to about 100° C., and most preferably about 20° C. to about 100° C.

Typically, the molar ratio of alpha-substituted acid chloride:disodium phenolsulfonate will be about 4:1 to about 1:4, and preferably about 2:1 to about 1:2. Most preferably, the molar ratio of alpha-substituted acid chloride:disodium phenolsulfonate is about 1:1.

Optional Components

As a preferred embodiment, the bleaching compositions of the invention can be formulated as laundry detergent compositions. Thus, the bleaching compositions can contain typical detergent composition components and adjuvants. Such components include detergency surfactants and detergency builders. When used in such embodiments the bleaching compositions are particularly effective.

The bleaching compositions of this invention can therefore contain all of the usual components of detergent compositions. This includes, without limitation, the ingredients set forth in U.S. Pat. No. 3,936,537, Baskerville, et al, issued Feb. 3, 1976, incorporated herein by reference. Such components, in addition to detergent surfactants and builders, include other peroxygen bleach activators, color speckles, suds boosters, suds suppressors, antitarnish and/or anticorrosion agents, soil-suspending agents, soil-release agents, dyes, fillers, optical brighteners, germicides, alkalinity sources, hydrotropes, antioxidants, enzymes, enzyme stabilizing agents, perfumes, etc.

Detergent Surfactants

The amount of detergent surfactant included in the detergent compositions of the present invention can vary from about 0% to about 75%, by weight of the composition, depending upon the detergent surfactant(s) used, the type of composition to be formulated (e.g. granular, liquid), the projected wash conditions and the effects desired. Preferably, the detergent surfactant(s) comprises from about 10% to about 50%, by weight, more preferably from about 1% to about 30%, and most preferably from about 10% to about 25%, by weight, of the total composition. However, because of the reactivity of the peroxygen bleach activator compounds of the present invention, liquid detergent compositions containing water should be formulated to stabilize these compounds.

The detergent surfactants which can be included in the bleaching compositions of the present invention include any one or more surface active agents selected from anionic, nonionic, zwitterionic, amphoteric and cationic surfactants, and compatible mixtures thereof. Detergent surfactants useful herein include, without limitation, those listed or described in U.S. Pat. No. 3,664,961, Norris, issued May 23, 1972, U.S. Pat. No. 3,929,678, Laughlin, et al, issued Dec. 30, 1975, U.S. Pat. No. 4,222,905, Cockrell, issued Sept. 16, 1980, and in U.S. Pat. No. 4,239,659, Murphy, issued Dec. 16, 1980, all incorporated herein by reference. The following are representative examples of detergent surfactants useful in the present compositions.

Anionic Surfactants

Anionic surfactants suitable in detergent compositions of the present invention are generally disclosed in U.S. Pat. No. 3,929,678 to Laughlin et al., issued Dec. 30, 1975 at column 23, line 56 through column 29, line 23 (incorporated herein by reference). Classes of anionic surfactants include the following.

Water-soluble salts of the higher fatty acids, i.e., "soaps", are useful anionic surfactants in the present compositions. This includes alkali metal soaps such as the sodium, potassium, ammonium, and alkylolammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Useful anionic surfactants also include the water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols (alcohols having from about 8 to about 18 carbon atoms) such as those produced by reducing the glycerides of tallow or coconut oil; the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383, are also useful. Especially useful are the linear straight chain alkylbenzene sulfonates in which the average number of carbon atoms in the alkyl group is from about 11 to 13 carbon atoms, often abbreviated as $C_{11-13}$LAS.

Other anionic surfactants useful in the bleaching compositions of the present invention are the sodium alkyl glyceryl ether sulfonates, especially those ethers (of higher alcohols) derived from tallow and coconut oil; the sodium coconut oil fatty acid monoglyceride sulfonates and sulfates; the sodium or potassium salts of alkyl phenol ethylene oxide ether sulfates containing from about 1 to about 10 units of ethylene oxide per molecule and wherein the alkyl groups contain from about 8 to about 12 carbon atoms; and the sodium or potassium salts of alkyl ethylene oxide ether sulfates containing about 1 to about 10 units of ethylene oxide per molecule and wherein the alkyl group contains from about 10 to about 20 carbon atoms.

Other anionic surfactants useful in the compositions of the present invention include the water-soluble salts of esters of alpha-sulfonated fatty acids containing from about 6 to 20 carbon atoms in the fatty acid group and from about 1 to 10 carbon atoms in the ester group; the water-soluble salts of 2-acyloxyalkane-1-sulfonic acids containing from about 2 to 9 carbon atoms in the acyl group and from about 9 to about 23 carbon atoms in the alkane moiety; the water-soluble salts of olefin and paraffin sulfonates containing from about 12 to 20 carbon atoms; and the beta-alkyloxy alkane sulfonates containing from about 1 to 3 carbon atoms in the alkyl group and from about 8 to 20 carbon atoms in the alkane moiety.

Nonionic Surfactants

Suitable nonionic surfactants for use in detergent compositions of the present invention are generally disclosed in U.S. Pat. No. 3,929,678 to Laughlin et al., issued Dec. 30, 1975 at column 13, line 14 through column 16, line 6 (herein incorporated by reference). Useful classes of nonionic surfactants useful in the compositions of the present invention include the following.

1. The polyethylene oxide condensates of alkyl phenols. These compounds include the condensation products of alkyl phenols having an alkyl group containing from about 6 to 12 carbon atoms in either a straight chain or branched chain configuration with ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene, and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by the GAF Corporation, and Triton X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol; and the condensation product of about 9 moles of ethylene oxide with coconut alcohol (a mixture of fatty alcohols with alkyl chains varying in length from 10 to 14 carbon atoms). Examples of commercially available nonionic surfactants of this type include Tergitol 15-S-9, marketed by Union Carbide Corporation, Neodol 45-9, Neodol 23-6.5, Neodol 45-7, and Neodol 45-4, marketed by Shell Chemical Company, and Kyro EOB, marketed by The Procter & Gamble Company.

3. The condensation products of ethylene oxide with a hydrophobic base formed by the condensation of propylene oxide with propylene glycol. The hydrophobic portion of these compounds has a molecular weight of from about 1500 to 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic surfactants, marketed by Wyandotte Chemical Corporation.

4. The condensation products of ethylene oxide with the product resulting from the reaction of propylene oxide and ethylenediamine. The hydrophobic moiety of these products consists of the reaction product of ethylenediamine and excess propylene oxide, the moiety having a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds, marketed by Wyandotte Chemical Corporation.

5. Semi-polar nonionic detergent surfactants which include water-soluble amine oxides containing one alkyl moiety of from about 10 to 18 carbon atoms and 2 moieties selected from the group consisting of alkyl groups and hydroxyalkyl groups containing from 1 to about 3 carbon atoms; water-soluble phosphine oxides containing one alkyl moiety of from about 10 to 18 carbon atoms and 2 moieties selected from the group consisting of alkyl groups and hydroxyalkyl groups containing from about 1 to 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Preferred semi-polar nonionic detergent surfactants are the amine oxide detergent surfactants having the formula

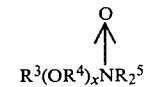

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from 2 to 3 carbon atoms or mixtures thereof; x is from 0 to about 3; and each $R^5$ is an alkyl or hydroxyalkyl group containing from 1 to about 3 carbon atoms or a polyethylene oxide group containing from one to about 3 ethylene oxide groups. The $R^5$ groups can be attached to each other, e.g., through an oxygen or nitrogen atom to form a ring structure.

Preferred amine oxide detergent surfactants are $C_{10}$–$C_{18}$ alkyl dimethyl amine oxide and $C_8$–$C_{12}$ alkoxy ethyl dihydroxy ethyl amine oxide.

6. Alkylpolysaccharides disclosed in U.S. application Ser. No. 371,747 Ramon A. Llenado, filed Apr. 26, 1982, having a hydrophobic group containing from about 6 to about 30 carbon atoms, preferably from about 10 to about 16 carbon atoms and a polysaccharide, e.g., a polyglycoside, hydrophilic group containing an average of from about 1½ to about 10, preferably from about 1½ to about 3, most preferably from about 1.6 to about 2.7 saccharide units. Any reducing saccharide containing 5 or 6 carbon atoms can be used, e.g. glucose, galactose and galactosyl moieties can be substituted for the glucosyl moieties. (Optionally the hydrophobic group is attached to other positions, e.g. the 2-, 3-, 4-, positions etc., thus giving a glucose or galactose as opposed to a glucoside or galactoside.) The intersaccharide bonds can be, for example between the 1-position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to 3 hydroxy groups and/or the polyalkyleneoxide chain can contain up to about 10, preferably less than 5, most preferably 0, alkyleneoxide moieties. Suitable alkyl polysaccharides are octyl, nonyl, decyl, undecyl, dodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and/or galactoses. Suitable mixtures include coconut alkyl, di-, tri-, tetra-, and pentaglucosides and tallow alkyl tetra-, penta-, and hexaglucosides.

The preferred alkylpolyglycosides have the formula

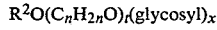
$R^2O(C_nH_{2n}O)_t(\text{glycosyl})_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from 1½ to about 10, preferably from about 1½ to about 3, most preferably from about 1.6 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

7. Fatty acid amide detergent surfactants having the formula:

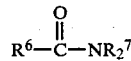
$$R^6-\overset{O}{\underset{\|}{C}}-NR_2^7$$

wherein $R^6$ is an alkyl group containing from about 7 to about 21 (preferably from about 9 to about 17) carbon atoms and each $R^7$ is selected from the group consisting of hydrogen, $C_1$-$C_4$ alkyl, $C_1$-$C_4$ hydroxyalkyl, and —$(C_2H_4O)_xH$ where x varies from about 1 to about 3.

Preferred amides are $C_8$-$C_{20}$ ammonia amides, monoethanolamides, diethanolamides, and isopropanol amides.

Ampholytic surfactants can be broadly described as derivatives of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group. See U.S. Pat. No. 3,929,678, Laughlin, et al., issued Dec. 30, 1975 at column 19, line 38 through column 22, line 48 for examples of ampholytic surfactants.

Zwitterionic Surfactants

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678, Laughlin, et al., issued Dec. 30, 1975 at column 19, line 38 through column 22, line 48 (incorporated herein by reference) for examples of zwitterionic surfactants.

Cationic Surfactants

Cationic surfactants can also be included in detergent compositions of the present invention. Suitable cationic surfactants include the quaternary ammonium surfactants having the formula:

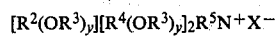
$[R^2(OR^3)_y][R^4(OR^3)_y]_2R^5N^+X^-$ wherein $R^2$ is an alkyl or alkyl benzyl group having from about 8 to about 18 carbon atoms in the alkyl chain; each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$-$C_4$ alkyl, $C_1$-$C_4$ hydroxyalkyl, benzyl, ring structures formed by joining the two $R^4$ groups, —$CH_2CHOH$-CHOHCO$R^6$CHOHCH$_2$OH wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is 0 to about 10 and the sum of the y values is from 0 to about 15; and X is any compatible anion.

Preferred of the above are the alkyl quaternary ammonium surfactants, especially the mono-long chain alkyl surfactants described in the above formula when $R^5$ is selected from the same groups as $R^4$. The most preferred quaternary ammonium surfactants are the chloride, bromide and methylsulfate $C_8$-$C_{16}$ alkyl trimethylammonium salts, $C_8$-$C_{16}$ alkyl di(hydroxyethyl)-methylammonium salts, the $C_8$-$C_{16}$ alkyl hydroxyethyl-dimethylammonium salts, and $C_8$-$C_{16}$ alkyloxypropyl trimethylammonium salts. Of the above, decyl trimethylammonium methylsulfate, lauryl trimethylammonium chloride, myristyl trimethylammonium methylsulfate and coconut trimethylammonium chloride and methylsulfate are particularly preferred. The use of bromides is least preferred due to the possible formation of hypobromite.

Detergent Builders

In addition to detergent surfactants, detergency builders can be employed in the bleaching compositions of the present invention. When included, the level of detergency builder of the bleaching compositions is from 0% to about 80%, preferably from about 10% to about 60%, by weight, and most preferably from about 20% to about 60%, by weight of the composition. Water-soluble inorganic or organic electrolytes are suitable builders. The builder can also be water-insoluble calcium ion exchange materials; nonlimiting examples of suitable water-soluble, inorganic detergent builders include: alkali metal carbonates, borates, phosphates, bicarbonates and silicates. Specific examples of such salts include sodium and potassium tetraborates, bicarbonates, carbonates, orthophosphates, pyrophosphates, tripolyphosphates and metaphosphates.

Suitable detergent builders include crystalline aluminosilicate ion exchange materials having the formula:

$$Na_z[(AlO_2)_z \cdot (SiO_2)_y] \cdot xH_2O$$

wherein z and y are at least about 6, the mole ratio of z to y is from about 1.0 to about 0.5; and x is from about 10 to about 264. Amorphous hydrated aluminosilicate materials useful herein have the empirical formula $$M_x(zAlO_2 \cdot ySiO_2)$$

wherein M is sodium, potassium, ammonium or substituted ammonium, z is from about 0.5 to about 2; and y is 1; this material having a magnesium ion exchange capacity of at least about 50 milligram.

The aluminosilicate ion exchange builder materials are in hydrated form and contain from about 10% to about 28% of water by weight if crystalline, and potentially even higher amounts of water if amorphous. Highly preferred crystalline aluminosilicate ion exchange materials contain from about 18% to about 22% water in their crystal matrix. The preferred crystalline aluminosilicate ion exchange materials are further characterized by a particle size diameter of from about 0.1 micron to about 10 microns. Amorphous materials are often smaller, e.g., down to less than about 0.01 micron. More preferred ion exchange materials have a particle size diameter of from about 0.2 micron to about 4 microns. The term "particle size diameter" represents the average particle size diameter of a given ion exchange material as determined by conventional analytical techniques such as, for example, microscopic determination utilizing a scanning electron microscope. The crystalline aluminosilicate ion exchange materials are usually further characterized by their calcium ion exchange capacity, which is at least about 200 mg. equivalent of $CaCO_3$ water hardness/g. of aluminosilicate, calculated on an anhydrous basis, and which generally is in the range of from about 300 mg. eq./g. to about 352 mg. eq./g. The aluminosilicate ion exchange materials are still further characterized by their calcium ion exchange rate which is at least about 2 grains $Ca^{++}$/gallon/minute/gram/gallon of aluminosilicate (anhydrous basis), and generally lies within the range of from about 2 grains/gallon/minute/gram)gallon to about 6 grains/gallon/minute/gram/gallon, based on calcium ion hardness. Optimum aluminosilicates for builder purposes exhibit a calcium ion exchange rate of at least about 4 grains/gallon/minute/gram/gallon.

The amorphous aluminosilicate ion exchange materials usually have a $Mg^{++}$ exchange capacity of at least about 50 mg. eq. $CaCO_3$/g. (12 mg. $Mg^{++}$/g.) and a $Mg^{++}$ exchange rate of at least about 1 grain/gallon/minute/gram/gallon. Amorphous materials do not exhibit an observable diffraction pattern when examined by Cu radiation (1.54 Angstrom Units).

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al., issued Oct. 12, 1976 (herein incorporated by reference). Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula $$Na_{12}[(AlO_2)_{12}(SiO_2)_{12}] \cdot xH_2O$$

wherein x is from about 20 to about 30, especially about 27.

Other examples of detergency builders include the various water-soluble, alkali metal, ammonium or substituted ammonium phosphates, polyphosphates, phosphonates, polyphosphonates, carbonates, silicates, borates, polyhydroxysulfonates, polyacetates, carboxylates, and polycarboxylates. Preferred are the alkali metal, especially sodium, salts of the above.

Examples of suitable organic alkaline detergency builders include: (1) water-soluble amino carboxylates and aminopolyacetates, for example, nitrilotriacetates, glycinates, ethylenediamine tetraacetates, N-(2-hydroxyethyl)nitrilo diacetates and diethylenetriamine pentaacetates; (2) water-soluble salts of phytic acid, for example, sodium and potassium phytates; (3) water-soluble polyphosphonates, including sodium, potassium and lithium salts of ethane-1-hydroxy-1, 1-diphosphonic acid; sodium, potassium, and lithium salts of ethylene diphosphonic acid; and the like; (4) water-soluble polycarboxylates such as the salts of lactic acid, succinic acid, malonic acid, maleic acid, citric acid, carboxymethyloxysuccinic acid, 2-oxa-1,1,3-propane tricarboxylic acid, 1,1,2,2-ethane tetracarboxylic acid, mellitic acid and pyromellitic acid; and (5) the water-soluble polyacetals as disclosed in U.S. Pat. Nos. 4,144,266 and 4,246,495, incorporated herein by reference.

Specific examples of inorganic phosphate builders are sodium and potassium tripolyphosphate, pyrophosphate, polymeric metaphosphate having a degree of polymerization of from about 6 to 21, and orthophosphate. Examples of polyphosphonate builders are the sodium and potassium salts of ethylene-1,1-diphosphonic acid, the sodium and potassium salts of ethane 1-hydroxy-1,1-diphosphonic acid and the sodium and potassium salts of ethane, 1,1,2-triphosphonic acid. Other phosphorus builder compounds are disclosed in U.S. Pat. Nos. 3,159,581; 3,213,030; 3,422,021; 3,422,137; 3,400,176 and 3,400,148 (all incorporated herein by reference).

Examples of nonphosphorus, inorganic builders are sodium and potassium carbonate, bicarbonate, sesquicarbonate, tetraborate decahydrate, and silicate having a mole ratio of $SiO_2$ to alkali metal oxide of from about 0.5 to about 4.0, preferably from about 1.0 to about 2.4.

Useful water-soluble, nonphosphorus organic builders include the various alkali metal, ammonium and substituted ammonium polyacetates, carboxylates, polycarboxylates and polyhydroxysulfonates. Examples of polyacetate and polycarboxylate builders are the sodium, potassium lithium, ammonium and substituted ammonium salts of ethylenediamine tetraacetic acid, nitrilotriacetic acid, oxydisuccinic acid, mellitic acid, benzene polycarboxylic acids, and citric acid.

Highly preferred polycarboxylate builders are disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other builders include the carboxylated carbohydrates disclosed in U.S. Pat. No. 3,723,322, Diehl, issued Mar. 28, 1973, incorporated herein by reference.

Other useful builders are sodium and potassium carboxymethyloxymalonate, carboxymethyloxysuccinate, cis-cyclohexanehexacarboxylate, cis-cyclopentanetetracarboxylate phloroglucinol trisulfonate, water-soluble polyacrylates (having molecular weights of from about 2,000 to about 200,000 for example), and the copolymers of maleic anhydride with vinyl methyl ether or ethylene.

Other suitable polycarboxylates are the polyacetal carboxylates disclosed in U.S. Pat. No. 4,144,226, Crutchfield, et al., issued Mar. 13, 1979, and U.S. Pat. No. 4,246,495, Crutchfield, et al., issued Mar. 27, 1979, both incorporated herein by reference. These polyacetal carboxylates can be prepared by bringing together under polymerization conditions an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Another type of detergency builder material useful in the present compositions comprises a water-soluble material capable of forming a water-insoluble reaction product with water hardness cations. This preferably occurs in combination with a crystallization seed which is capable of providing growth sites for said reaction product. Such "seeded builder" compositions are fully disclosed in British Patent Specification No. 1,424,406, incorporated herein by reference. Other useful detergency builder materials are the "seeded builder" compositions disclosed in Belgian Pat. No. 798,856, issued Oct. 29, 1973, incorporated herein by reference. Specific examples of such seeded builder mixtures are: 3:1 wt. mixtures of sodium carbonate and calcium carbonate having 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

Additional Optional Components

Buffering agents can be utilized to maintain the desired alkaline pH of the bleaching solutions. Buffering agents include, without limitation, the detergency builder compounds disclosed herein. Buffering agents suitable for use in the bleaching compositions of the present invention are well known in the detergency art.

Preferred optional ingredients include suds modifiers, particularly those of suds suppressing types. These include, for example, silicones and silica-silicone mixtures. U.S. Pat. Nos. 3,933,672, issued Jan. 20, 1976 to Bartolotta et al, and 4,136,045, issued Jan. 23, 1979 to Gault et al, incorporated herein by reference, disclose silicone suds controlling agents. The silicone material can be represented by alkylated polysiloxane materials such as silica aerogels and xerogels and hydrophobic silicas of various types. The silicone material can be described as siloxane having the formula:

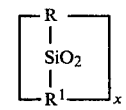

where x is from about 20 to about 2,000 and R and $R^1$ are each alkyl or aryl groups, especially methyl, ethyl, propyl, butyl and phenyl. The polydimethylsiloxanes (i.e., compounds of the above formula wherein R and $R^1$ are methyl) having a molecular weight of from about 200 to about 2,000,000 (and higher) are all useful as suds controlling agents. Additional suitable silicone materials wherein the side chain groups R and $R^1$ are alkyl, aryl, or mixed alkyl or aryl hydrocarbyl groups, exhibit useful suds controlling properties. These include diethyl-, dipropyl-, dibutyl-, methyl-, ethyl-, phenylmethyl-poly-siloxanes, and the like. Additional useful silicone suds controlling agents can be represented by a mixture of an alkylated siloxane, as referred to hereinbefore, and solid silica. Such mixtures are prepared by affixing the silicone to the surface of the solid silica. A preferred silicone suds controlling agent is represented by a hydrophobic silanated (most preferably trimethylsilanated) silica having a particle size in the range from about 10 millimicrons to 20 millimicrons and a specific surface area above about 50 m²/gm. intimately admixed with dimethyl silicone fluid having a molecular weight in the range from about 500 to about 200,000 at a weight ratio of silicone to silanated silica of from about 19:1 to about 1:2. The silicone suds suppressing agent is advantageously releasably incorporated in a water-soluble or water-dispersible, substantially non-surface-active detergent-impermeable carrier.

Particularly useful suds suppressors are the self-emulsifying silicone suds suppressors, described in U.S. Pat. No. 4,073,118, Gault et al, issued Feb. 21, 1978, incorporated herein by reference. An example of such a compound is DB-544, commercially available from Dow-Corning, which is a siloxane/glycol copolymer.

Suds modifiers as described above are used at levels of 0% to about 2%, preferably from about 0.1 to about 1.5% by weight of the surfactant.

Microcrystalline waxes having a melting point in the range from 35° C.–115° C. and a saponification value of less than 100 represent additional examples of preferred suds control components for use in the bleaching compositions of the present invention. These are described in detail in U.S. Pat. No. 4,056,481, Tate, issued Nov. 1, 1977, incorporated herein by reference. The microcrystalline waxes are substantially water-insoluble, but are water-dispersible in the presence of organic surfactants. Preferred microcrystalline waxes have a melting point from about 65° C. to 100° C., a molecular weight in the range from 400–1,000, and a penetration value of at least 6, measured at 77° F. by ASTM-D1321. Suitable examples of the above waxes include: microcrystalline and oxidized microcrystalline petroleum waxes; Fischer-Tropsch and oxidized Fischer-Tropsch waxes; ozokerite; ceresin; montan wax; beeswax; candelilla; and carnauba wax.

Alkyl phosphate esters represent an additional preferred suds control agent for use herein. These preferred phosphate esters are predominantly monostearyl phosphate which, in addition thereto, can contain di- and tristearyl phosphates and monooleyl phosphate, which can contain di- and trioleyl phosphate.

Other suds control agents useful in the practice of the invention are the soap or the soap and nonionic mixtures as disclosed in U.S. Pat. Nos. 2,954,347 and 2,954,348, incorporated herein by reference.

The following examples are given to illustrate the parameters of and compositions within the invention. All percentages, parts and ratios are by weight unless otherwise indicated.

EXAMPLE I

The following bleaching/granular detergent compositions and systems were formulated using conventional procedures and techniques. When employed in conventional procedures for overall performance testing (such as the described in Example I of U.S. Pat. No. 4,412,934, Chung, et al., issued Nov. 1, 1983) or in typical washing procedures, excellent bleaching performance is obtained.

| | BLEACH COMPOSITIONS/SYSTEMS |
|---|---|
| A | Sodium perborate alone |
| B | Sodium perborate monohydrate |
|   | Sodium 4-(2-chlorobutanoyloxo)benzene sulfonate |
| C | Sodium perborate monohydrate |
|   | Sodium 4-(2-chlorooctanoyloxo)benzene sulfonate |
| D | Sodium perborate monohydrate |
|   | Sodium 4-(2-chlorononanoyloxo)benzene sulfonate |
| E | Sodium perborate monohydrate |
|   | Sodium 4-(2-chlorodecanoyloxo)benzene sulfonate |
| F | Sodium perborate monohydrate |
|   | Sodium 4-(3,5,5-trimethyl-2-chlorohexanoyloxo)benzene sulfonate |
| G | Sodium perborate monohydrate |
|   | Sodium 4-(2-chloro-2-ethylhexanoyloxo)benzene sulfonate |
| H | Sodium perborate monohydrate |
|   | Sodium 2-(2-chlorononanoyloxo)benzoate |
| I | Sodium perborate monohydrate |
|   | Sodium 4-(2-methoxydecanonyloxo)benzene sulfonate |
| J | Sodium perborate monohydrate |
|   | Sodium 4-(2-methoxydodecanonyloxo)benzene sulfonate |

The following granular detergent composition is prepared to be used with the above indicated systems and other bleach compositions of the present invention:

| | Parts by Weight |
|---|---|
| Sodium $C_{14-15}$ alkyl/alkylethoxy sulfate | 8.75 |
| $C_{12-13}$ linear alkyl primary alcohol ethoxylate$_{6.57}$* | 8.75 |
| $C_{12}$ alkyltrimethyl ammonium chloride | 1.0 |
| Sodium tripolyphosphate | 37.0 |
| Sodium diethylenetriamine penta-acetate | 1.0 |
| Sodium carbonate | 14.0 |
| Sodium sulfate | 11.5 |
| Silicon dioxide (SiO$_2$) (1.6r) | 6.0 |
| Water | 7.0 |
| Bleach Composition C | 12.0 |
| Miscellaneous (e.g., perfumes, enzymes, suds supressors, optical brighteners, etc.) | 1.8 |

*Stripped of lower ethoxylated fractions and fatty alcohol.

The above granular detergent composition is used employing 12 parts of the bleach composition for each treatment at the suggested ratios. All ingredients of the final detergent composition are added to the wash simultaneously. The overall order of addition is water-fabrics-test composition. In some cases, the activator may be dissolved in water before addition.

Bleach Composition C in the detergent composition above is replaced, in whole or in part, by Bleach Compositions D–J, or mixtures thereof, and similar bleaching performance is obtained. Further, various ratios of perborate (total):bleach activator (total), by weight of the composition, may be employed: 1:1, 3:1, 1:2, 1:3 and 6:5; good bleaching performance is obtained at these ratios for single systems, and for mixtures of such systems.

The peroxygen bleach activator compounds of the above systems and Bleach Compositions are replaced, in part, by a second conventional activator, at a ratio of alpha substituted peroxygen bleach activator:second activator of about 3:1 to about 1:3. When such conventional activator is selected from the group consisting of sodium 4-octanoyloxybenzenesulfonate; sodium 4-nonanoyloxybenzenesulfonate; tetra acetyl glycouril; tetra acetyl ethylene diamine; and tetra acetyl methylene diamine, similar bleaching performance is obtained.

The sodium perborate monohydrate of the above Bleach Compositions and systems is replaced, in whole or in part, at a perborate (total):bleach activator ratio of about 1:3 to about 3:1, by one or more peroxygen bleach compounds selected from the group consisting of sodium perborate tetrahydrate; sodium carbonate peroxyhydrate; sodium pyrophosphate peroxyhydrate, urea peroxyhydrate, and sodium peroxide; similar bleaching performance is obtained.

EXAMPLE II

Preparation of Bodies Containing Peroxygen Bleach Activator 87 parts of the selected peroxygen bleach activator ingredient (alpha-substituted alkyl oxybenzene sulfonate) is thoroughly mixed with the binder or coating (Sorbitan monopalmitate) in a warm container 70°–75° C. (160°–170° F.) until a homogeneous doughy consistency is achieved. This mixture is then forced through a warmed 70°–75° C. (160°–170° F.) orifice (approximately 1.5 mm diameter) to produce long noodles. After cooling to room temperature these are then cut into 1.5–3 mm lengths and screened (24 mesh) to remove fine particulate matter and dust resulting from the cutting operation. The final material is then added to, mixing thoroughly, a granular detergent composition such as that described in Example I.

The binder material above is replaced, in whole or in part, by $C_{13}$LAS, $C_{12}$LAS, $C_{11}$LAS, sorbitan monolaurate, sorbitan monostearate, sorbitan monooleate, a 1:1 mixture (by weight) of PEG 8000:lauric acid, sodium polyacrylate and sodium methacrylate; similar stability is obtained.

EXAMPLE III

Preparation of Disodium p-Phenolsulfonate

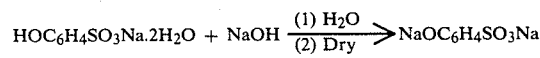

Disodium p-phenolsulfonate was prepared by adding a solution of 483.5 g (12.1 moles) of sodium hydroxide in 750 ml of water to 2784 g (12.0 mole) of the monosodium salt dihydrate dispersed in 2 l. of water. The final pH of this mixture was 10.6. Most of the water was evaporated in a rotary evaporator and the resulting rigid solid was transferred to a vacuum oven for final drying at 115°–120° C. (100 hours in this example). The anhydrous disodium salt weighed 2607 g (99.6% yield).

Preparation of Sodium 4-(2-chlorooctanoyloxy)benzene sulfonate

Anhydrous disodium p-phenolsulfonate (221 g; 1.015 moles) was slurried in 500 ml of dry diglyme (diethylene glycol dimethylether) in a 1 l, three-necked flask equipped with a mechanical stirrer, thermometer and an inert gas inlet. This mixture was warmed to 48° C. and 200 g (1.015 moles) of 2-chlorooctanoyl chloride was added, dropwise or in a thin stream, at such a rate that the temperature did not rise substantially above 100° C. The reaction mixture was cooled occasionally during the acid chloride addition. After the acid chloride had been added, the mixture was stirred for two hours at which time a thin layer chromatogram and a proton nmr spectrum showed that the reaction was essentially complete.

The thick mixture was then diluted with ether to give an easily pourable slurry which was filtered. The product (filter cake) was reslurried in 1.5 l of ether and filtered again. Recrystallization from 3.5 l of 20% aqueous methanol gave 280 g (77% yield) of sodium 4-(2-chlorooctanoyloxy)benzene sulfonate as lustrous white flakes. By thin layer chromatography, infrared and nmr spectroscopy the product was virtually free of starting materials or side products. Elemental analysis indicated it contained 0.44% NaCl.

EXAMPLE IV

Preparation of Sodium 4-(decanoyloxy)benzene sulfonate

Decanoyl chloride (19.1 g; 0.10 mole) was added all at once to a slurry of 21.8 g (0.10 mole) of anhydrous disodium phenolsulfonate and 50 ml of dry monoglyme contained in a 500 ml round-bottomed flask protected from moisture. A modest exotherm occurred and the reaction mixture was stirred at ambient temperature overnight. A thin layer chromatogram indicated that the reaction was essentially complete, and the thick creamy mixture was diluted with ether and filtered. The solids were rinsed with additional ether, were sucked dry, and the product was then recrystallized from 500 ml of 10% aqueous methanol. The sodium p-decanoyloxybenzene sulfonate was collected by filtration and dried to give 34.6 g (99%) of pearly flakes. Elemental, thin layer chromatographic, infrared and nuclear magnetic resonance analyses indicated that the product was essentially free of sodium chloride, starting materials or other by-products.

EXAMPLE V

Preparation of Sodium 4-(2-chlorononanoyloxy)benzene sulfonate

Anhydrous disodium p-phenolsulfonate (28.5 g; 0.130 mole) and 30.3 g (0.1436 mole) of 2-chlorononanoyl chloride were combined in a 500 ml round-bottomed flask. The flask was then immersed in an oil bath which had been preheated to 110° C. Within five minutes an exothermic reaction occurred which caused the entire mixture to congeal. After cooling, the mixture was triturated three times with 150–200 ml portions of ether and the product was vacuum dried. Elemental and nmr analyses of the resulting tan powder, 46.2 g, indicated that it was composed of 11.5% NaCl, 17.7% disodium p-phenolsulfonate, and 70.8% of sodium p-(2-chlorononanoyloxy)benzene sulfonate. This represents a 68% yield of the desired product.

EXAMPLE VI

Preparation of 2-Chloroalkyl Acid

A one-liter, three-necked round bottom reaction flask was mounted in a fume hood and placed in a 335 watt heating mantle. A mechanical stirrer, dry ice condenser and a fritted gas dispersion tube were fitted to the reaction flask. The temperature of the reaction flask was controlled by use of a Thermo-Watch which maintains the function of a Jack-O-Matic, upon which the heating mantle was placed. The dispersion tube was connected to a chlorine source by PVC tubing and metered with an in line flowmeter having a range of 0.05 to 1 liter/min.

The reaction vessel was initially charged with 1.0 mole of stearic acid (284.5 grams). The stearic acid was melted by raising the temperature to 80° C. At this time 0.005 mole TCNQ (1.02 grams) was added to the reaction vessel. Chlorine gas at a flow rate of 0.05 liter/min. was added to solubilize the TCNQ into the melted stearic acid. Acetic anhydride at a 0.06 molar level (6.125 grams) was then added to the reaction flask and the temperature was rapidly elevated to 130° C. Using a pipette, 0.016 mole sulfuric acid (1.6 grams) was then added to the reaction vessel. The temperature was then adjusted to 150° C. and the chlorine flow rate was adjusted to 0.5 liter/min. This point was considered time zero for the beginning of the reaction.

After 52 minutes of reaction time, the chlorine flow rate was readjusted to 0.05 liter/min. and the reaction mixture was slowly cooled under a head of chlorine gas to the product melting point (64° C.).

After cooling, the reaction product was analyzed by gas chromatography as being 96.12% 2-chlorostearic acid, 2.71% 2,2-dichlorostearic acid, 0.42% free radical chlorination products, and 0.75% unreacted stearic acid.

If the above reaction is carried out with fatty acids having alkyl chain lengths from 8 to 18 carbons, or combinations thereof, the corresponding 2-chloroalkyl acids are produced in purities exceeding 95%. These materials may then be employed as follows:

Preparation of 4-(2-chlorononanoyloxy)benzenesulfonate

The reaction was carried out in a 12 l flask equipped with a heavy duty paddle stirrer, reflux condenser, addition funnel, thermometer, heating mantle and inert gas inlet.

A slurry of 2237 g (10.26 moles) of disodium p-phenolsulfonate in a gallon of dry 1,2-dimethoxyethane (monoglyme) was warmed to 50° C. The heating mantle was switched off and the addition of 2169 g (10.28 moles) of 2-chlorononaoyl chloride was begun. The rate of addition was such that a steady reflux was maintained. As the reaction proceeded, it thickened and after 80 minutes, with about 80-85% of the acid chloride added, another 500 ml of solvent was added to improve stirring. The acid chloride addition was complete within 1.5 hours after which the mixture was allowed to stand overnight.

Ether (3 l) was added to give a thinner slurry and the crude product was collected by vacuum filtration. By nmr, the crude product contained 88 mole percent product and 12 mole percent starting phenolsulfonate (plus salts).

Recrystallization was carried out, batchwise, from a total of 65 l of 12.5% aqueous methanol at 5° C. There was obtained 2672 g (70% yield) of first crop product as lustrous white flakes. Concentration of the mother liquor followed by another recrystallization gave a second crop (330 g) which brought the recovered yield to 79%.

What is claimed is:

1. A peroxygen bleach activator comprising a compound of the general formula

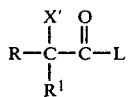

where R is a straight or branched chain alkyl or alkenyl containing from about 4 to about 14 carbon atoms, $R^1$ is H, $CH_3$, $C_2H_5$ or $C_3H_7$, X' is Cl, $OCH_3$ or $OC_2H_5$, and L is a leaving group the conjugate acid of which has a $pK_a$ of about 4 to about 30.

2. A compound according to claim 1 wherein X' is Cl.

3. A compound according to claim 1 wherein L is selected from the group consisting of:

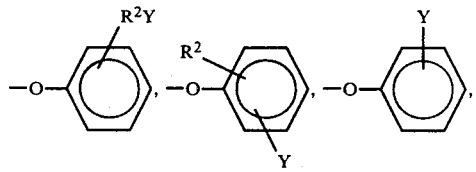

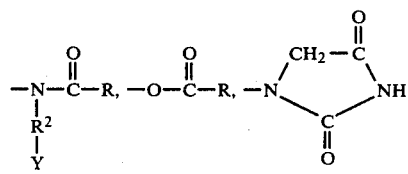

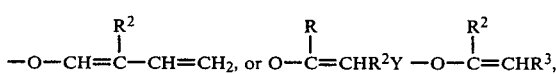

wherein R and $R^1$ are as defined in claim 1, X is Cl, $R^2$ is an alkyl chain containing from about 1 to about 8 carbon atoms, $R^3$ is H or $R^2$, and Y is H or a solubilizing group.

4. A compound according to claim 3 wherein Y is selected from the group consisting of: $—SO_3^-M^+$, $—COO^-M^+$, $—SO_4^-M^+$, $(—N^+R_3^4)X^-$ and $O\leftarrow NR_2^4$ and mixtures thereof, wherein $R^4$ is an alkyl chain containing from about 1 to about 4 carbon atoms, M is a cation, and X is an anion such that M and X together provided solubility to the bleach activator.

5. A compound according to claim 4 wherein Y is selected from the group consisting of $—SO_3^-M^+$, $—COO^-M^+$, and mixtures thereof, wherein M is selected from the group consisting of sodium, potassium and mixtures thereof.

6. A compound according to claim 3 wherein L is selected from the group consisting of:

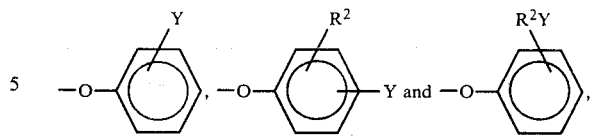

$R^2$ is an alkyl chain containing from about 1 to about 8 carbon atoms, and Y is $—SO_3^-M^+$ or $—COO^-M^+$ wherein M is sodium or potassium.

7. A compound according to claim 6 wherein L has the formula:

and M is sodium or potassium.

8. A compound according to claim 3 wherein R is a linear alkyl group containing from about 6 to about 10 carbon atoms and $R^1$ is H.

9. A compound according to claim 8 wherein R is a linear alkyl chain containing from about 6 to about 8 carbon atoms.

10. A compound according to claim 3 wherein R is a linear alkyl chain containing from about 6 to about 8 carbon atoms and $R^1$ is $C_2H_5$.

11. A compound according to claim 3 wherein R is a branched alkyl chain containing from about 6 to about 12 carbon atoms wherein the longest linear alkyl portion of said chain contains from about 4 to about 10 carbon atoms, and L is selected from the group consisting of:

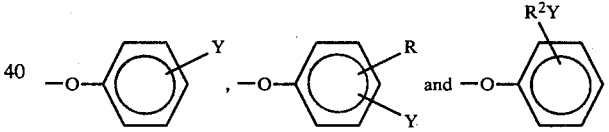

wherein $R^2$ is an alkyl chain containing from about 1 to about 8 carbon atoms, and Y is $—SO_3^-M^+$ or $—COO^-M^+$ wherein M is sodium or potassium.

12. A compound according to claim 11 wherein the longest linear alkyl portion of R contains from about 4 to about 8 carbon atoms.

13. A compound according to claim 8 wherein L has the general formula

wherein M is sodium or potassium.

14. A compound according to claim 11 wherein L has the general formula

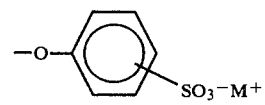

wherein M is sodium or potassium.

15. A peroxygen bleach activator comprising a compound of the general formula

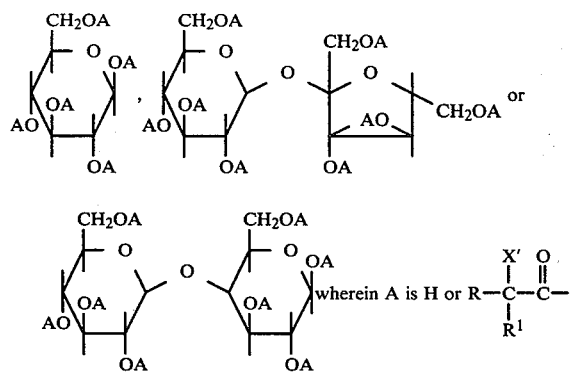

wherein R is a branched or linear alkyl or alkenyl group having from about 4 to about 14 carbon atoms; $R^1$ is H, $CH_3$, $C_2H_5$ or $C_3H_7$; and X' is Cl, $OCH_3$ or $OC_2H_5$; provided that at least one A is not H.

16. A compound according to claim 15 wherein no A is H.

17. A bleaching composition comprising:
(a) a peroxygen bleach compound capable of yielding hydrogen peroxide in an aqueous solution; and
(b) a bleach activator compound according to claim 1 wherein the ratio of (a):(b) is about 10:1 to about 1:4, by weight of the composition.

18. A composition according to claim 17 wherein the ratio of (a):(b) is from about 3:1 to about 1:2, by weight of the composition.

19. A composition according to claim 18 wherein the ratio of (a):(b) is from about 3:1 to about 1:1, by weight of the composition.

20. A composition according to claim 17 wherein the peroxygen bleaching compound is selected from the group consisting of sodium perborate monohydrate, sodium perborate tetrahydrate, sodium carbonate peroxyhydrate, sodium pyrophosphate peroxyhydrate, urea peroxyhydrate, sodium peroxide and mixtures thereof.

21. A composition according to claim 20 wherein the peroxygen bleaching compound is sodium perborate monohydrate.

22. A bleaching composition comprising, by weight:
(a) from about 1% to about 60% of a peroxygen bleaching compound capable of yielding hydrogen peroxide in an aqueous solution;
(b) from about 1% to about 30% of a detergent surfactant;
(c) from about 0.5% to about 40% of a bleach activator compound according to claim 2.

23. The composition of claim 22 further comprising from about 10% to about 60% of a detergency builder.

24. A composition according to claim 23 wherein the bleach activator is selected from the group consisting of sodium 4-(2-chlorooctanoyloxy)benzenesulfonate, sodium 4-(2-chlorononanoyloxy)benzenesulfonate, sodium 4-(2-chlorodecanoyloxy)benzenesulfonate, sodium 4-(3,5,5-trimethyl-2-chlorohexanoyloxy)benzene sulfonate, sodium 4-(2-chloro-2-ethyl-hexanoyloxy)benzenesulfonate, sodium 2-(2-chlorooctanoyloxy)benzenesulfonate, sodium 2-(2-chlorononanoyloxy)benzene sulfonate, sodium 2-(2-chlorooctanoyloxy)benzoate, sodium 2-(2-chlorononanoyloxy)benzoate, sodium 4-(2-chlorooctanoyloxy)benzoate, and sodium 4-(2-chlorononanoyloxy)benzoate, and mixtures thereof.

* * * * *

UNITED STATES PATENT AND TRADEMARK OFFICE
CERTIFICATE OF CORRECTION

PATENT NO. : 4,483,778
DATED : November 20, 1984
INVENTOR(S) : James E. Thompson; Charles D. Broaddus It is certified that error appears in the above-identified patent and that said Letters Patent are hereby corrected as shown below:

Column 36, line 40

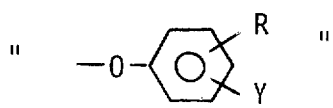

should be

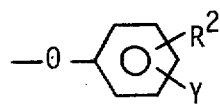

Signed and Sealed this

Twelfth Day of November 1985

[SEAL]

Attest:

DONALD J. QUIGG

Attesting Officer

Commissioner of Patents and Trademarks